United States Patent [19]

Nakabayashi et al.

[11] Patent Number: 5,368,733
[45] Date of Patent: Nov. 29, 1994

[54] WATER-SOLUBLE CELLULOSE DERIVATIVE AND BIOCOMPATIBLE MATERIAL

[75] Inventors: Nobuo Nakabayashi, Matsudo; Kazuhiko Ishihara, Kodaira, both of Japan

[73] Assignee: NOF Corporation, Tokyo, Japan

[21] Appl. No.: 133,167

[22] PCT Filed: Feb. 12, 1993

[86] PCT No.: PCT/JP93/00177
  § 371 Date: Oct. 13, 1993
  § 102(e) Date: Oct. 13, 1993

[87] PCT Pub. No.: WO93/16117
  PCT Pub. Date: Aug. 19, 1993

[30] Foreign Application Priority Data

Feb. 13, 1992 [JP] Japan ............... 4-058763

[51] Int. Cl.$^5$ .............................. B01D 69/08
[52] U.S. Cl. .............. 210/500.23; 106/163.1; 210/500.29
[58] Field of Search ............. 210/490, 500.23, 500.29; 106/163.1, 177

[56] References Cited

U.S. PATENT DOCUMENTS 4,792,599 12/1988 Durrani .................. 528/272

FOREIGN PATENT DOCUMENTS 57-43563 9/1982 Japan .

Primary Examiner—Frank Spear
Attorney, Agent, or Firm—Darby & Darby

[57] ABSTRACT

A water-soluble cellulose derivative which is obtained by subjecting a water-soluble cellulose to graft polymerization with 2-methacryloyloxyethyl phosphorylcholine and has a structural unit of the following formula (I):

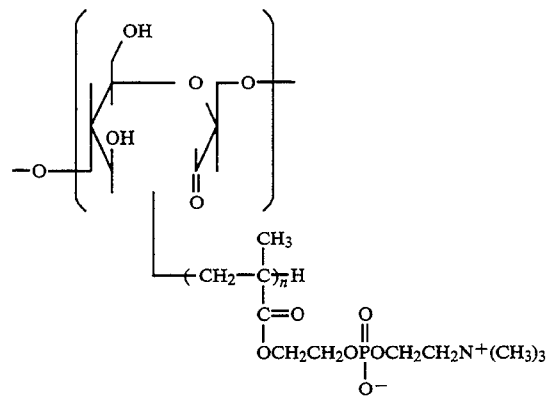

wherein n is an integer of 1–100, as well as a biocompatible material containing the water-soluble cellulose derivative as an effective component thereof. The water-soluble cellulose derivative having such specific structural unit is furnished with both of biocompatibility and affinity to cellulose and is thus utilizable as a biocompatible material, for example for hemocatharsis.

6 Claims, 2 Drawing Sheets

— 10 μm

——— 50 μm

——— 50 μm

— 10 μm

— 10 μm

WATER-SOLUBLE CELLULOSE DERIVATIVE AND BIOCOMPATIBLE MATERIAL

FIELD OF ART

The present invention relates to a novel water-soluble cellulose derivative and a blood-compatible material possessing biocompatibility such as excellent blood-compatibility and the like.

BACKGROUND ART

Hemocatharsis including hemodialysis, hemofiltration, etc. are employed at present as apothanasia for patients of chronic renal insufficiency, and the number of patients in our country to whom hemocatharsis is applied already exceeds 100,000. The principle of hemocatharsis resides in contact of blood with a dialyzing liquid through a thin membrane thereby eliminating spodogen and metabolites by diffusion into the dialyzing liquid and also removal of excess water by utilizing difference in hydraulic pressure. In case hemocatharsis is to be carried out, a hemocathartic vessel is used where a blood circuit made of a bundle of hollow fibers is accommodated in a housing to have a structure wherein blood flows inside the hollow fibers while the dialyzing liquid flows outside the hollow fibers.

An anti-coagulant such as heparin has hitherto been continuously administered in case of hemocatharsis with a view of inhibiting coagulation reaction of blood in the hemocathartic vessel. Now that long-term apothanacia as long as 20 years has become possible according to an improvement in elimination performance of solutes in the hemocathartic vessel, problems caused by the use of heparin are successively pointed out. In particular, hepatic disorder, such as lipid metabolism abnormality, elongation of bleeding time or allergic reactions due to the administration of heparin for a long period of time, is recognized to be side effect for patients. From these viewpoints, development of a biocompatible material is demanded which is so excellent in blood-compatibility that coagulation of blood is not caused by a little or no use of an anti-coagulant in case of hemocathartic therapy.

As an attempt to improve blood-compatibility of cellulose hollow fibers, for example, reports have been made regarding inhibition of activation of complements contained in cellulose membrane materials due to a method for covalently bonding a hydrophilic high polymer such as polyethylene oxide to the surface of the fibers or a method for treating the surface with a high polymer containing tertiary amino groups, etc. However, it is difficult to inhibit coagulation of blood in such hollow fibers so that administration of a large amount of an anti-coagulant becomes eventually necessary. Thus, development of such a substance itself is demanded which is furnished with both affinity to cellulose as a base and biocompatibility.

It is an object of the present invention to provide a novel water-soluble cellulose derivative possessing both biocompatibility and affinity to cellulose.

It is another object of the present invention to provide a biocompatible material which is excellent in biocompatibility and utilizable for hemocathartic vessels and the like.

DISCLOSURE OF THE INVENTION

Figure 1:
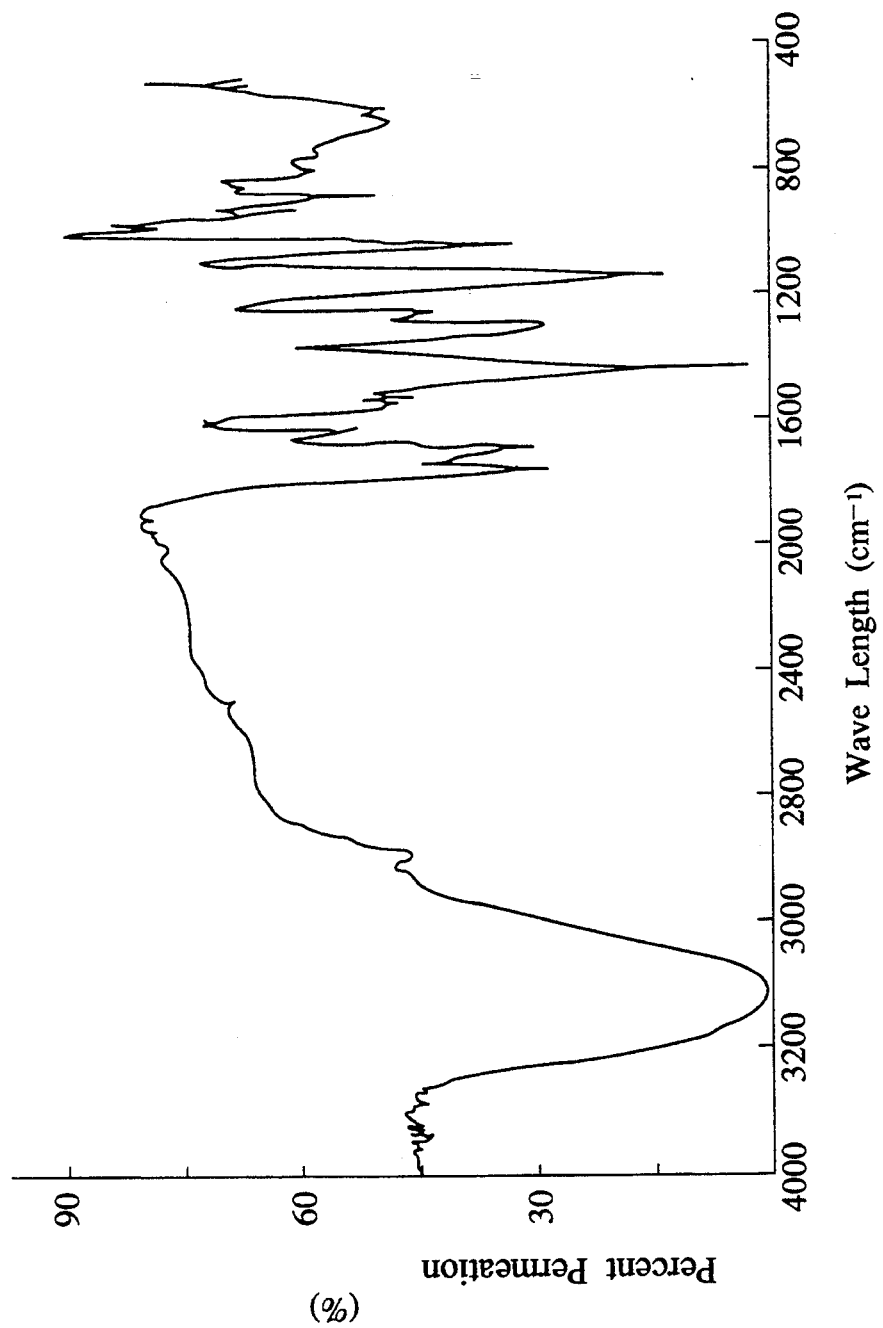
FIG. 1 is a graph showing an IR-absorption spectrum of an MPC-grafted cellulose as prepared in Example 1.

In accordance with the present invention, there is provided a water-soluble cellulose derivative having a structural unit of the following formula (I):

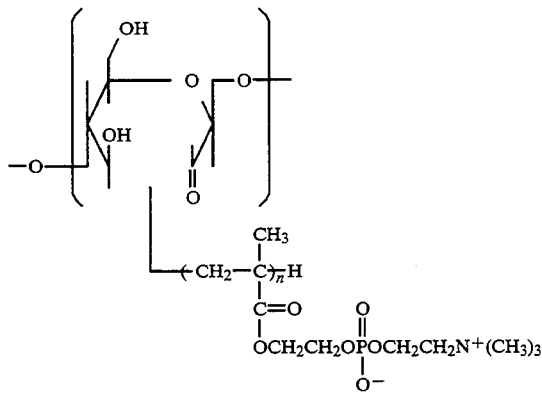

wherein n stands for an integer of 1–100, obtained by graft polymerization of a soluble cellulose with 2-methacryloyloxyethyl phosphorylcholine (referred to hereinafter as MPC).

In accordance with the present invention, there is also provided a biocompatible material including the above water-soluble cellulose derivative as an effective component.

BEST MODES FOR CARRYING OUT THE INVENTION

The present invention is explained further in detail hereinbelow.

The water-soluble cellulose derivative of the present invention is a polymer having the structural unit of the above formula (I) obtained by graft polymerization of a water-soluble cellulose with MPC wherein n in the above formula (I) stands for an integer of 1–100, preferably 1–30. It is preferred that the molecular weight of the water-soluble cellulose derivative according to gel permeation chromatography (referred to hereinafter as GPC) be within the range of $1.0 \times 10^4$–$1.0 \times 10^6$ in terms of polyethylene glycol. If the molecular weight is less than $10 \times 10^4$, the derivative fails to form a stable film in case of being used as biocompatible materials, whereas if the molecular weight exceeds $1.0 \times 10^6$, its solubility in water becomes poor, thus being not preferred. It is preferable that the amount of MPC to be graft-polymerized to the water-soluble cellulose be 5–70% by weight based on the whole amount of the water-soluble cellulose. If the amount is less than 5% by weight, the material shows inferior antithrombotic properties when used an antithrombotic materials, whereas if the amount exceeds 70% by weight, affinity to the cellulose is reduced, thus being preferred.

The water-soluble cellulose used for preparing the water-soluble cellulose derivative of the present invention be obtained, for example by a known method wherein cellulose microcrystals are subjected to hydrolysis simultaneously with acetylation with acetic anhydride-sulfuric acid followed by deacetylation in the presence of an alkali ("Cellulose Handbook" compiled by Hiroshi Sofue and published by Asakura Bookstore, 1958). On the other hand, MPC can be obtained, for example by a known method wherein a condensate of 2-hydroxyethyl methacrylate with 2-chloro-2-oxo-1,3,2-dioxaphosphorane is reacted in acetonitrile with trimethylamine at 60° C. for 15 hours ["Polym., J., 22 355–360 (1990)].

The graft polymerization reaction of MPC to the water-soluble cellulose for preparing the water-soluble cellulose derivative of this invention is desirably carried out, for example by effecting polymerization in an aqueous solution system using a cerium ion-containing compound or a peroxide such as hydrogen peroxide as an initiator capable of forming radicals on the water-soluble cellulose. The polymerization temperature is preferably within the range of 30°–65° C., more preferably 40°–50° C. for inhibiting decomposition of cellulose and homopolymerization of MPC and for forming radicals on the cellulose. The polymerization time is preferably within the range from 30 minutes to 3 hours, and is particularly desirable within the range of 1–2 hours considering the yield of graft polymerization for MPC. Further, the amount of MPC to be charged for the graft polymerization is preferably 10–1000 times (weight ratio) based on the water-soluble cellulose. In case the charged amount of MPC is less than 10 times, it is impossible to obtain the grafted amount of MPC, for example, for exhibiting biocompatibility, whereas if the amount exceeds 1000 times, the amount of MPC homopolymer formed is extremely increased, thus being not preferred.

There is no special limitation to the shade of the biocompatible materials of this invention, so far as it contains the water-soluble cellulose derivative as an effective component thereof. For example, it may be used in the form of a film or the like. More precisely, a method wherein an aqueous solution of the water-soluble cellulose derivative diluted to a predetermined concentration is prepared and then dried in vacuum For 1–24 hours at about room temperature after being passed through the hollow fibers made of cellulose or the like method is used to prepare a film on the inner surface of the hollow fibers, which is utilizable as a living body liquid-compatible material for blood or the like. An aqueous solution per se of the water-soluble cellulose derivative may be used according to a known method for forming hollow fibers or biomembrane.

The water-soluble cellulose derivative of the present invention possessing both biocompatibility and affinity to cellulose is useful as a starting material for various biocompatible materials. The biocompatible material of the present invention containing the water-soluble cellulose derivative as an effective component thereof is excellent in biocompatibility and utilizable for hemocathartic vessels and the like.

EXAMPLES

The present invention will now be illustrated more in detail by way of examples and comparative examples. It is construed, however, that the present invention is not limited to these.

EXAMPLE 1

Grafting Reaction of MPC to Cellulose

In a mixed liquid of 38 ml of acetic anhydride and 38 ml of glacial acetic acid was dispersed 10 g of finely divided powders of cellulose. After addition of 4 ml of concentrated sulfuric acid, the mixture was stirred for one hour at 50° C. to obtain a transparent liquid. The resultant transparent liquid was then added dropwise to acetone for reprecipitation. After low molecular weight compounds were removed and dried in vacuum, 9.5 g of acetylcellulose was obtained. To 2.5 g of the resultant acetylcellulose were added 50 ml of an aqueous solution of 1N-sodium carbonate and 100 ml of an aqueous solution of 3N-sodium hydroxide, and the mixture was stirred to effect deacetylation. Hydrochloric acid was then added to the reaction liquid for neutralization, and the solution was placed in a dialyzing membrane. The solution was dialyzed for 3 days against water to eliminate low molecular substances, thereby obtaining an aqueous solution of a water-soluble cellulose. A part of the solution was taken to determine the weight concentration of the cellulose by drying it by heating, and the solution was diluted with water to make its 0.5% by weight solution. To 10 ml of this solution were added 0.17 g of ammonium cerium nitrate, 3 ml of 1N-nitric acid and further 0.9 g of MPC, and the air was replaced by argon for 10 minutes. The container was tightly sealed and the mixture was stirred for one hour at 40° C. to effect graft polymerization. After completion of the reaction, the mixture was placed in a dialyzing membrane and dialyzed against water to purify MPC-grafted cellulose. FIG. 1 shows an IR-absorption spectrum of the MPC-grafted cellulose thus obtained. As a result of quantitatively determining phosphorus, the amount of MPC-grafted to cellulose was found to be 10.1% by weight. The molecular weight of the product obtained by way of gel permeation chromatography was found to be $1.2 \times 10^5$ in terms of polyethylene glycol.

EXAMPLES 2–5

Reaction was carried out in the same manner as described in Example 1 except that the amount of MPC charged was varied as shown in Table 1, and each MPC-grafted water-soluble cellulose was obtained. Table 1 shows the amount of MPC grafted and a result of the measurement of molecular weight.

TABLE 1

| A result of synthesis of MPC-grafted water-soluble cellulose | | |
| --- | --- | --- |
| MPC (g) | Weight % of MPC-grafted | Molecular Weight ($\times 10^5$) |
| Example 2  1.2 | 11.3 | 1.4 |

TABLE 1-continued

A result of synthesis of MPC-grafted
water-soluble cellulose

| | MPC (g) | Weight % of MPC-grafted | Molecular Weight ($\times 10^5$) |
|---|---|---|---|
| Example 3 | 1.8 | 17.4 | 1.3 |
| Example 4 | 2.4 | 23.8 | 1.2 |
| Example 5 | 3.0 | 37.5 | 1.4 |

EXAMPLES 6-9

Each aqueous solution of the MPC-grafted cellulose prepared in Examples 2-5 was passed at a flow rate of 5 ml/min. through a hollow fiber (inner diameter: 200 μm, length: 10 cm made of regenerated cellulose prepared according to the cupraammonium method. After each hollow fiber was allowed to stand for 10 minutes in the state being filled inside with the aqueous solution of the MPC-grafted cellulose, the solution was expelled by air and the fiber was immediately dried in vacuum for 20 hours at room temperature. Table 2 shows the amount of MPC-grafted cellulose thus coated.

TABLE 2

A result of coating hollow fiber made of
cellulose with 0.5% by weight aqueous
solution of MPC-grafted cellulose

| | Cellulose used | Amount of cellulose coated ($\mu g/cm^2$) |
|---|---|---|
| Example 6 | Example 2 | 8.6 |
| Example 7 | Example 3 | 6.3 |
| Example 8 | Example 4 | 12.6 |
| Example 9 | Example 5 | 10.4 |

EXAMPLES 10-12

Coating of the hollow fiber with the MPC-grafted cellulose was carried out in the same manner as described in Examples 6-9 except that aqueous solutions of MPC-grafted cellulose shown in Table 3 were used at a concentration of 1.0% by weight and that the velocity of passing through the hollow fiber was 10 ml/min. Table 3 shows the amount of the MPC-grafted cellulose thus coated.

TABLE 3

A result of coating hollow fiber made
of cellulose with 1.0% by weight aqueous
solution of MPC-grafted cellulose

| | Cellulose used | Amount of cellulose coated ($\mu g/cm^2$) |
|---|---|---|
| Example 10 | Example 1 | 8.9 |
| Example 11 | Example 3 | 10.2 |
| Example 12 | Example 5 | 12.7 |

EXAMPLES 13-18, COMPARATIVE EXAMPLES 1 AND 2

Figure 2:
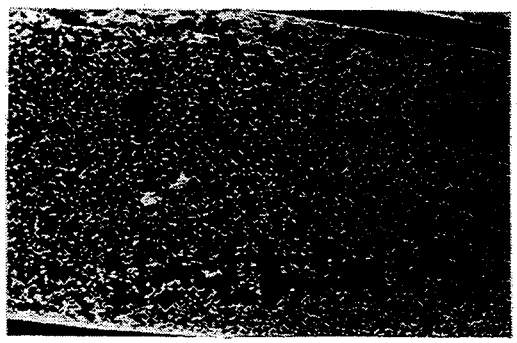
FIG. 2 is a photograph of the inner surface of untreated cellulose hollow fibers taken by a scanning electron microscope after allowing a thrombocyte-enriched plasma to pass through the inside of the fibers for 60 minutes.
Figure 3:
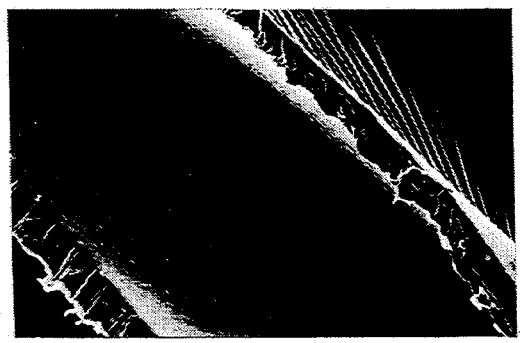
FIG. 3 is a photograph of the inner surface of cellulose hollow fibers coated with a biocompatible material of the present invention taken by a scanning electron microscope after allowing a thrombocyte-enriched plasma to pass through the inside of the fibers for 60 minutes.

Evaluation of Blood-compatibility 480 hollow fibers made of cellulose, the inner surface of which had been coated with the MPC-grafted cellulose shown in Table 4 (Examples 13-16), or 480 untreated hollow fibers made of cellulose, the inner surface of which had not been coated with the MPC-grafted cellulose (Comparative Example 1), were respectively bundled into modules (total membrane area: 0.1 m²). Fresh blood extracted from carotid arteries of a house rabbit with the use of sodium citrate (0.38%) as an anti-coagulant was passed through each module for one hour at a flow rate of 0.5 ml/min. After the inside of the hollow fibers were then rinsed with physiological saline, the hollow fibers were filled with physiological saline containing 1.25% of glutaraldehyde, and the fibers were allowed to stand for 2 hours. The inside of the modules was replaced by purified water and the whole was freeze dried. After vacuum evaporation of gold, the inside of the hollow fibers was observed with a scanning electron microscope (SEM) and the number of adhering thrombocytes was measured. A result of the measurement is shown in Table 4. FIGS. 2 and 3 show SEM photographs relating to Example 16 and Comparative Example 1, respectively.

TABLE 4

A result of experiments on thrombocytes
adhering to hollow fibers made of cellulose

| | Hollow fiber used | Number of adhering thrombocyte (cells/mm²) |
|---|---|---|
| Example 13 | Example 6 | 0 |
| Example 14 | Example 8 | 0 |
| Example 15 | Example 11 | 0 |
| Example 16 | Example 12 | 0 |
| Comparative Example 1 | Untreated hollow fibers made of cellulose | $7.98 \times 10^4$ |

Figure 4:
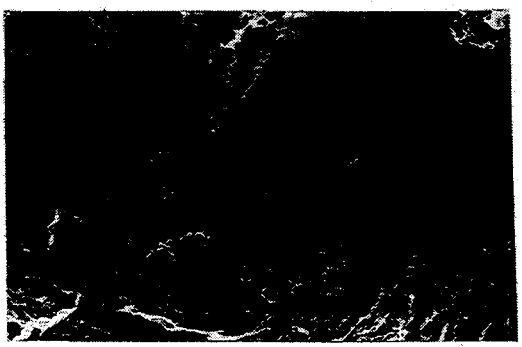
FIG. 4 is a photograph of the inner surface of untreated cellulose hollow fibers taken by a scanning electron microscope after allowing the whole blood to pass through the inside of the fibers.
Figure 5:
FIG. 5 is a photograph of the inner surface of cellulose hollow fibers coated with the biocompatible material of the present invention taken by a scanning electron microscope after allowing the whole blood to pass through the inside of the fibers.

480 hollow fibers made of cellulose, the inner surface of which had been coated with the MPC-grafted cellulose shown in Table 5 (Examples 17 and 18), or 480 untreated hollow fibers made of cellulose, the inner surface of which had not been coated with the MPC-grafted cellulose (Comparative Example 2), were respectively bundled into modules, each of which was then connected to a blood circuit formed between a carotid artery and a cervical vein of a house rabbit. A flow of blood was adjusted so that the flow rate of blood became 2 ml/min. The tinge required until coagulation of the blood in the hollow fibers was measured in the state of administering no anti-coagulant. Table 5 shows a result of the measurement. After completion of the experiments, the inner surface of the hollow fibers was observed by SEM according to the same operation as described above. FIGS. 4 and 5 show SEM photographs relating to Example 18 and Comparative Example 2, respectively.

TABLE 5

Time required until coagulation of whole
blood in hollow fibers

| | Hollow fiber used | Coagulation time |
|---|---|---|
| Example 17 | Example 9 | >60 min. |
| Example 18 | Example 12 | >60 min. |
| Comparative Example 2 | Untreated hollow fiber made of cellulose | 40 min. |

EXAMPLES 19-21 AND COMPARATIVE EXAMPLE 3

Measurement for Permeation of Substances

Dialyzing performance of each of urea and creatinine was measured. In case of urea, an aqueous solution of urea of 200 mg/dl was prepared, and 480 hollow fibers made of cellulose, the inner surface of which had been coated with the MPC-grafted cellulose shown in Table 6 (Examples 19-21), or 480 untreated hollow fibers made of cellulose, the inner surface of which had not been coated with the MPC-grafted cellulose (Comparative Example 3), were respectively bundled into modules. The solution was then allowed to pass through each module of the hollow fibers for 60 minutes. 30 ml of pure water was circulated around the outside of the hollow fibers in each module and the amount of urea permeated through the hollow fibers was checked. In case of creatinine, on the other hand, its solution of 26 mg/dl was used and the permeated amount was calculated according to the same operation as in the case of urea. Table 6 shows a result of the experiments.

| Initial Concentration of $H_2S$ (ppm) | Outlet Concentration of $H_2S$ (ppm) | Removal Ratio (%) |
| --- | --- | --- |
| 1800 | 67.5 | 96.1 |
| 900 | 20.1 | 97.7 |
| 350 | 0.0 | 100.0 |

We claim:

1. A water-soluble cellulose derivative having a structural unit of the following formula (I):

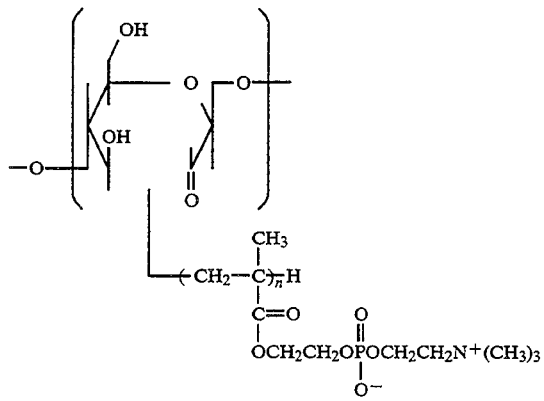

wherein n stands for an integer of 1–100, obtained by graft polymerization of a soluble cellulose with 2-methacryloyloxyethyl phosphorylcholine.

2. A water-soluble cellulose derivative according to claim 1, wherein a molecular weight of the water-soluble cellulose derivative according to gel permeation chromatography is $1.0 \times 10^4 - 1.0 \times 10^6$ in terms of polyethylene glycol.

3. A water-soluble cellulose derivative according to claim 1, wherein an amount of 2-methacryloyloxyethyl phosphorylcholine in the water-soluble cellulose derivative is 5–70% by weight based on a whole amount of the water-soluble cellulose derivative.

4. A water-soluble cellulose derivative according to claim 1, wherein an amount of 2-methacryloyloxyethyl phosphorylcholine to be charged for graft-polymerization of 2-methacryloyloxyethyl phosphorylcholine to the water-soluble cellulose is 10–1000 times by weight ratio to the water-soluble cellulose.

5. A biocompatible material containing the water-soluble cellulose derivative according to claim 1 as an effective component.

6. A biocompatible material according to claim 5, wherein the biocompatible material is a membrane formed on an inner surface of a hollow fiber.

* * * * *